United States Patent [19]

Sugimori et al.

[11] 4,405,488

[45] Sep. 20, 1983

[54] LIQUID-CRYSTALLINE HALOGENOBENZENE DERIVATIVES

[75] Inventors: Shigeru Sugimori; Tetsuhiko Kojima; Masakazu Tsuji, all of Yokohamashi, Japan

[73] Assignee: Chisso Corporation, Osaka, Japan

[21] Appl. No.: 302,517

[22] Filed: Sep. 16, 1981

[30] Foreign Application Priority Data

| Oct. 9, 1980 | [JP] | Japan | 55-141536 |
| Oct. 14, 1980 | [JP] | Japan | 55-143394 |
| Oct. 24, 1980 | [JP] | Japan | 55-149053 |
| Oct. 29, 1980 | [JP] | Japan | 55-151772 |
| Jan. 7, 1981 | [JP] | Japan | 56-1029 |
| Jan. 7, 1981 | [JP] | Japan | 56-1030 |
| Feb. 14, 1981 | [JP] | Japan | 56-20566 |
| Mar. 4, 1981 | [JP] | Japan | 56-30812 |
| Mar. 13, 1981 | [JP] | Japan | 56-36148 |
| Mar. 28, 1981 | [JP] | Japan | 56-46065 |
| Apr. 8, 1981 | [JP] | Japan | 56-52566 |
| Apr. 9, 1981 | [JP] | Japan | 56-53700 |

[51] Int. Cl.³ .................... G02F 1/13; C09K 3/34; C07C 25/18
[52] U.S. Cl. .................... 252/299.63; 252/299.5; 252/299.6; 252/299.66; 350/350 R; 570/129; 570/182; 570/188
[58] Field of Search ............ 252/299.5, 299.6, 299.63, 252/299.66; 350/350 R; 570/129, 182, 188

[56] References Cited

U.S. PATENT DOCUMENTS

| 4,130,502 | 12/1978 | Eidenschink et al. | 252/299.63 |
| 4,154,697 | 5/1979 | Eidenschink et al. | 252/299.63 |
| 4,181,625 | 1/1980 | Eidenschink et al. | 252/299.63 |
| 4,211,666 | 7/1980 | Inukai et al. | 252/299.6 |
| 4,302,352 | 11/1981 | Eidenschink et al. | 252/299.63 |
| 4,330,426 | 5/1982 | Eidenschink et al. | 252/299.5 |
| 4,331,552 | 5/1982 | Eidenschink et al. | 252/299.5 |
| 4,340,498 | 7/1982 | Sugimori | 252/299.5 |
| 4,368,138 | 1/1983 | Osman | 252/299.5 |

FOREIGN PATENT DOCUMENTS

| 19665 | 12/1980 | European Pat. Off. | 252/299.63 |
| 51738 | 5/1982 | European Pat. Off. | 252/299.63 |
| 62470 | 10/1982 | European Pat. Off. | 252/299.63 |
| 2933563 | 2/1981 | Fed. Rep. of Germany | 252/299.63 |
| 2939782 | 4/1981 | Fed. Rep. of Germany | 252/299.64 |
| 2949080 | 6/1981 | Fed. Rep. of Germany | 252/299.62 |
| 3006666 | 9/1981 | Fed. Rep. of Germany | 252/299.6 |
| 53-82676 | 7/1978 | Japan | 252/299.5 |
| 53-82679 | 7/1978 | Japan | 252/299.68 |
| 54-148184 | 11/1979 | Japan | 252/299.63 |
| 56-150030 | 11/1981 | Japan | 252/299.66 |
| 57-40429 | 3/1982 | Japan | 252/299.66 |
| 57-165326 | 10/1982 | Japan | 252/299.63 |
| 2039937 | 8/1980 | United Kingdom | 252/299.66 |
| 2078727 | 1/1982 | United Kingdom | 252/299 |

OTHER PUBLICATIONS

Karamysheva, L. A. et al., Advances in Liquid Crystal Research & Applications, Data, L., Pergamon Press, Oxford, pp. 997–1002 (1980).

Demus, D. et al., Flüssige Kristalle in Tabellen, Veb Deutscher Verlag, Leipzig, pp. 34–36 (1974).

Gray, G. W., Mol. Cryst. Liq. Cryst., vol. 63, pp. 3–18 (1981).

Gray, G. W. et al., Mol. Cryst. Liq. Cryst., vol. 67, pp. 1–24 (1981).

Gray, G. W. et al., Mol. Cryst. Liq. Cryst., vol. 53, pp. 147–166 (1979).

*Primary Examiner*—Teddy S. Gron
*Attorney, Agent, or Firm*—Wenderoth, Lind & Ponack

[57] ABSTRACT

New liquid crystal compounds having a low viscosity and nevertheless having a high transparent point and a broad nematic temperature range, and liquid crystal compositions containing the same are provided. The compounds are liquid-crystalline halogenobenzene derivatives expressed by the general formula

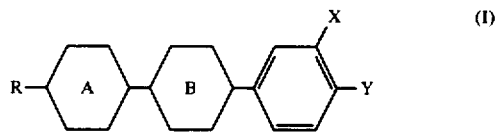

wherein R represents an alkyl group having 1 to 10 carbon atoms;

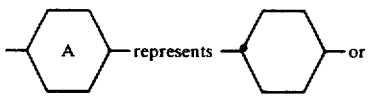

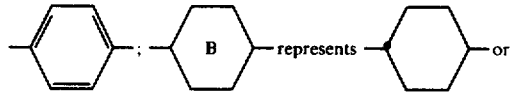

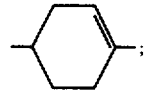

and X and Y each are H, F or Cl, at least one of X and Y being F or Cl.

9 Claims, No Drawings

LIQUID-CRYSTALLINE HALOGENOBENZENE DERIVATIVES

BACKGROUND OF THE INVENTION

This invention relates to a novel liquid crystal substance having a positive dielectric anisotropy.

Liquid crystal display elements utilize optical anisotropy and dielectric anisotropy of liquid crystal substances, and are classified by their display modes into various types such as TN type (twisted nematic type), DS type (dynamic scattering type), guest-host type, DAP type, etc.; and the properties of liquid crystal substances suitable to their respective uses are different. However, it is common to any of such liquid crystal substances that they must to be stable to moisture, air, heat, light, etc., and also, there is a need for those which exhibit a liquid crystal phase within as broad a temperature range as possible, centering at room temperature. However, no single compounds satisfying such requirements have been found to date, and it is the present status that liquid crystal compositions obtained by mixing together several kinds of liquid crystal compounds and non-liquid crystal compounds have been used. In particular, liquid crystal display elements actuated within a temperature range as broad as $-30°$ to $+100°$ C. have come to be required. In order to satisfy such requirements, it is effective to reduce their viscosities, particularly those at lower temperatures. Generally, however, those having a higher transparent point (N-I point) have higher viscosity, while those having a lower viscosity such as alkylphenylcyclohexane derivatives have a lower transparent point.

Thus, the object of the present invention is to provide novel liquid crystal compounds which have a higher transparent point in spite of their lower viscosity and also have a broad nematic temperature range, and liquid crystal compositions containing the same.

SUMMARY OF THE INVENTION

The present invention resides in:
liquid-crystalline halogenobenzene derivatives expressed by the general formula

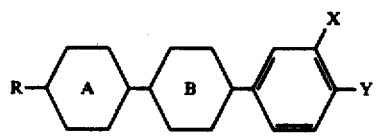

wherein R represents an alkyl group having 1 to 10 carbon atoms;

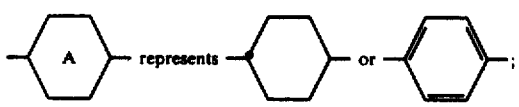

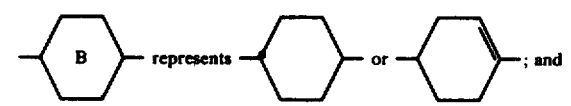

X and Y each are H, F or Cl, at least one of X and Y being F or Cl,
and liquid crystal compositions containing at least one of the above derivatives.

DESCRIPTION OF THE PREFERRED EMBODIMENTS

The compounds of the present invention have low viscosities, as low as about 20 to 30 cp at 20° C.; nevertheless they have nematic temperature ranges as broad as 50° to 150° C.; and moreover have high transparent points. Thus they are very useful compounds as components constituting liquid crystal compositions used for liquid crystal display cells actuated within a temperature range from lower temperatures to higher ones. Further, the compounds have a dielectric anisotropy $\Delta\epsilon$ of about +0.2 to 4, and nevertheless the threshold voltages and saturation voltages of liquid crystal compositions having the compounds incorporated therein do not rise so much as compared with those not having the compounds incorporated therein, but are almost the same as the latter. Furthermore, compounds having

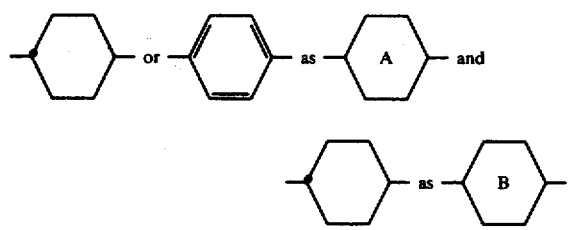

in the above general formula (I) are extremely stable to heat, light, air, moisture, etc. and can be incorporated into almost all kinds of liquid crystal compositions; hence the application range of the compounds is broad.

Next the method of preparing the compounds of the present invention expressed by the general formula (I) will be mentioned.

First, in the case of preparing compounds having

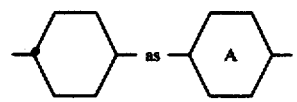

in the formula (I), a 4-(trans-4'-alkylcyclohexyl)phenol is reduced with a Raney nickel catalyst in ethanol at 100° C. to 140° C. under a hydrogen pressure of 20 to 40 Kg/cm²G for 6 to 12 hours to obtain a 4-(trans-4'-alkylcyclohexyl)cyclohexanol, which is a cis-trans mixture relative to the cyclohexane ring having the OH group attached thereto.

On the other hand, in the case of preparing compounds having

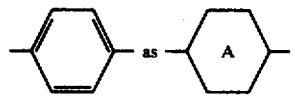

in the formula (I), a 4-alkyl-4'-hydroxybiphenyl is reduced with a Raney nickel catalyst in ethanol at a temperature of 80° to 120° C. under a hydrogen pressure of 30 to 40 Kg/cm²G for 3 to 7 hours, followed by reacting the resulting material with metallic sodium and isolating a trans-4-(4'-alkylphenyl)cyclohexanol as product.

The product obtained above

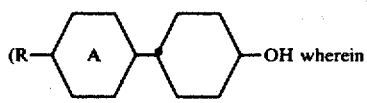 wherein

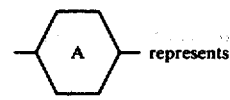 represents

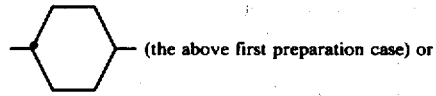 (the above first preparation case) or (the above second preparation case)) is oxidized with chromic anhydride to obtain a 4-(4'-alkylcyclohexyl)cyclohexanone or a 4-(4'-alkylphenyl)cyclohexanone.

On the other hand, a 3,4-halogen-substituted-bromobenzene is reacted with metallic magnesium to obtain a 3,4-halogen-substituted-phenylmagnesium bromide which is then reacted with the 4-substituted cyclohexanone prepared above to obtain a 3,4-halogen-substituted-(4-substituted-cyclohexane-1'-ol)benzene.

This derivative is then dehydrated in the presence of potassium hydrogen sulfate as catalyst to obtain a 3,4-halogen-substituted-(4'-substituted-cyclohexen-1'-yl)benzene (a compound having

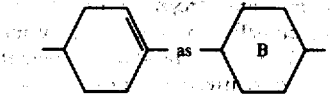

in the formula (I)), which is then hydrogenated in the presence of platinum oxide as catalyst in benzene or toluene to obtain a 3,4-halogen-substituted-(trans-4'-substituted-cyclohexyl)benzene (a compound having

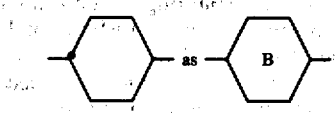

in the formula (I).

The foregoing reactions will be illustrated by chemical formulas as follows:

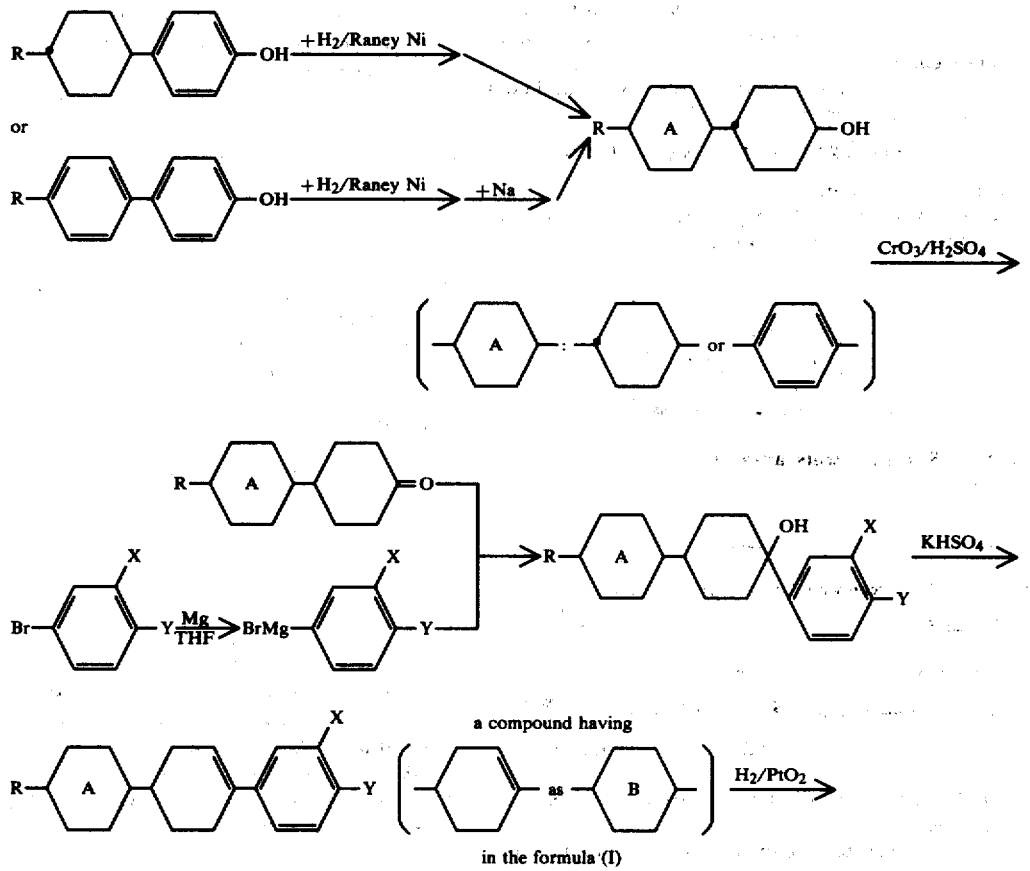

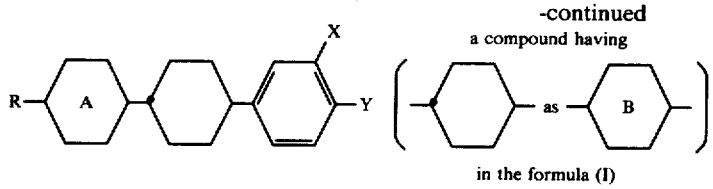

a compound having $$\left( -\underset{}{\bigcirc}- as -\underset{B}{\bigcirc}- \right)$$

in the formula (I)

The preparation and properties of the compounds of the present invention will be further mentioned in more details by way of Examples.

EXAMPLE 1

Preparation of 4-[4'-(trans-4''-propylcyclohexyl)cyclohexen-1'-yl]fluorobenzene (a compound of the formula (I) wherein R: C₃H₇,

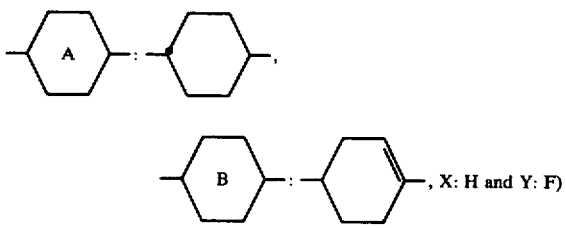

, X: H and Y: F)

Raney nickel (20 g) was added to 4-(trans-4-propylcyclohexyl)phenol (200 g) and further ethanol (1.8 l) was added to dissolve the phenol. The resulting solution containing Raney nickel had hydrogen absorbed in a proportion of 3 mols based on one mol of the phenol, at 100° to 120° C. under hydrogen pressures of 30 to 40 Kg/cm²G for 8 hours (this period being indicated by gas chromatography carried out during the reaction through extinction of the phenol). After completion of the hydrogenation, the catalyst was filtered off and ethanol was completely distilled off to give 4-(trans-4'-propylcyclohexyl)cyclohexanols which are a trans-cis mixture relative to the cyclohexanol ring (160 g, yield: 80.7%). Fifty grams of this product was suspended in 1.5 l of acetone and while the suspension was kept at −3° to 0° C., a solution obtained by adding water to chromic anhydride (14.5 g) and conc. sulfuric acid (23.6 g) so as to give a volume of 50 ml, was dropwise added to the suspension over 2 hours. After completion of the reaction, the excess amount of the oxidizing agent was decomposed by adding isopropyl alcohol, followed by further adding sodium hydrogen carbonate to render the solution neutral, whereby a precipitate formed, which was washed with 200 ml of acetone, followed by combining the material with the filtrate obtained above, distilling off acetone from the combination under reduced pressure and then extracting it three times with 500 ml of toluene. The resulting toluene layers were combined together and dried over anhydrous sodium sulfate, followed by distilling off toluene under reduced pressure and subjecting the residue to vacuum distillation to collect a fraction of 160°∼166° C./3 mmHg, which was recrystallized from ethanol to give crystals of 4-(trans-4'-proplycyclohexyl)cyclohexanone (m.p.: 24.4°∼25.3° C., Yield: 40.0 g, 80.7%).

On the other hand, a piece of magnesium (1.2 g, 0.049 mol) was placed in a three-neck flask, and 25 ml of a solution obtained by dissolving 4-fluorobromobenzene (8.6 g, 0.049 mol) in tetrahydrofuran was slowly and dropwise added to the magnesium in nitrogen gas current while the reaction temperature was kept at 30°∼35° C., during which magnesium dissolved in 3 hours to obtain a uniform solution of 4-fluorobenzenemagnesium bromide. To this bromide was dropwise and as fast as possible added a solution obtained by dissolving 9.0 g (0.041 mol) of 4-(trans-4'-propylcyclohexyl)cyclohexanone obtained above in tetrahydrofuran so as to give a volume of 50 ml, while the reaction temperature was kept at 5°∼10° C. After the addition, the temperature was raised up to room temperature, followed by stirring for one hour and then adding 100 ml of 3 N hydrochloric acid. The reaction liquid was taken in a separating funnel and three times extracted with 100 ml of toluene. The resulting toluene layers were combined together and washed with a saturated aqueous solution of sodium chloride until the washing solution became neutral, followed by distilling off toluene under reduced pressure. The resulting oily substance as residue was 4-[4'-(trans-4''-propylcyclohexyl)-cyclohexan-1'-ol]fluorobenzene. To this product was added 2.0 g of potassium hydrogen sulfate, followed by dehydration in nitrogen gas current at 150° C. for one hour. After cooling, 200 ml of toluene was added, potassium hydrogen sulfate was filtered off and the toluene layer was washed with water until the washing solution became neutral, followed by distilling off toluene under reduced pressure and then recrystallizing an oily substance as residue from ethanol to give the objective 4-[4'-(trans-4''-propylcyclohexyl)cyclohexen-1'-yl]fluorobenzene, which was a nematic liquid crystal having a m.p. (C-N point) of 58.8°∼59.7° C. and a transparent point (N-I point) of 150.0° C. Yield: 1.0 g (6.8%). Its elemental analysis values accorded nearly with the calculated values as follows:

| | Analytical values (%) | Calculated values |
|---|---|---|
| C | 84.0 | 83.9 |
| H | 9.6 | 9.7 |

Further it was also evidenced through its NMR spectra to correspond to the objective compound.

EXAMPLES 2∼10

Compounds were prepared the same as in Example 1 except that, in the formula (I), R (alkyl) was varied from that of Example 1 (Examples 2∼5) and further, Y in the formula (I) was changed from F to Cl (Examples 6∼10). Their yields (g, %) and phase transition points are shown together with those of Example 1 in Table 1.

TABLE 1

| Example | In Formula (I)*1 | | | Yield | | Phase transition points (°C.)*2 | | |
|---|---|---|---|---|---|---|---|---|
| | R | X | Y | (g) | (%) | C-N point or C-S point | S-N point | N-I point |
| 1 | C₃H₇ | H | F | 1.0 | 6.8 | 58.8∼59.7 | — | 150 |
| 2 | C₄H₉ | H | F | 3.5 | 22.7 | 68.8∼69.7 | — | 146∼ |

TABLE 1-continued

| Example | In Formula (I)[1] R | X | Y | Yield (g) | (%) | Phase transition points (°C.)[2] C-N point or C-S point | S-N point | N-I point |
|---|---|---|---|---|---|---|---|---|
| 3 | C5H11 | H | F | 0.9 | 5.5 | 57.2~58.9 | — | 148.1 145.1~146.9 |
| 4 | C6H13 | H | F | 0.5 | 20 | 87.8~88.6 | — | 158.5 |
| 5 | C7H15 | H | F | 0.6 | 17 | 53.9~56.1 | — | 143.9 |
| 6 | C3H7 | H | Cl | 5.0 | 32 | 105.3~106.6 | — | 189.3~189.8 |
| 7 | C4H9 | H | Cl | 4.5 | 28 | 56.0 | 73.2~74.2 | 183.4 |
| 8 | C5H11 | H | Cl | 3.9 | 23 | 88.8~89.0 | — | 184.5 |
| 9 | C6H13 | H | Cl | 4.5 | 26 | 52.2 | 66.0~67.6 | 178.3 |
| 10 | C7H15 | H | Cl | 4.3 | 23 | 82.4 | — | 174.4 |

[1]All compounds of these examples have

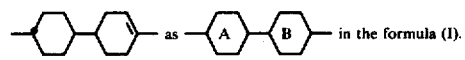 as 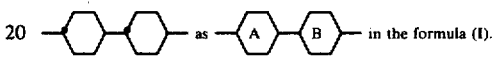 in the formula (I).

[2]Symbols C, N, S and I represent solid phase, nematic phase, smetic phase and transparent phase, respectively.

EXAMPLE 11

Preparation of 4-[trans-4'-(trans-4"-propylcyclohexyl)cyclohexyl]fluorobenzene (a compound of the formula (I) wherein R:C3H7,

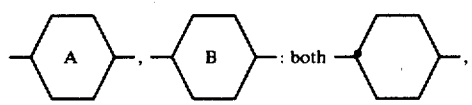

X:H and Y:F)

4-[4'-(trans-4"-propylcyclohexyl)cyclohexen-1'-yl]fluorobenzene prepared in Example 1 (1 g) was dissolved in benzene (10 ml), and platinum oxide (0.2 g) was added as catalyst, followed by catalytic reduction at 30° C. under atmospheric pressure while passing hydrogen gas therethrough. As briefly described in Example 1, since the reduction of benzene as solvent also proceeds at the same time, the raw material and the product were both traced by gas chromatography and when the raw material was extinct, that is, after 15 hours, the reduction reaction was completed. At that time, the amount of hydrogen absorbed was 2.23 l. The catalyst was filtered off and the solvent was distilled off under reduced pressure, followed by recrystallizing crystals as residue from ethanol to obtain crystals of the objective 4-[trans-4'-(trans-4"-propylcyclohexyl)cyclohexyl]fluorobenzene (0.3 g). The yield was 30% based on the raw material prior to the catalytic reduction. Its physical properties (phase transition points) are shown in Table 2. Further, its NMR spectra were not inconsistent with the fact that the product corresponded to the objective compound.

EXAMPLES 12~20

4-[4'-(Trans-4"-alkylcyclohexyl)cyclohexen-1'-yl]-halogenobenzenes obtained in Examples 2~10 were reduced as in Example 11 to obtain the corresponding 4-[trans-4'-(trans-4"-alkylcyclohexyl)cyclohexyl]-halogenobenzenes. Their yields, phase transition points, etc. are shown together with those of Example 11 in Table 2.

TABLE 2

| Example | In Formula (I)* R | X | Y | Yield (g) | (%) | Phase transition point (°C.) C-N point or C-S point | S-N point | N-I point |
|---|---|---|---|---|---|---|---|---|
| 11 | C3H7 | H | F | 0.3 | 30 | 87.8~88.6 | — | 158.5 |
| 12 | C4H9 | H | F | 0.25 | 25 | 79.6~80.6 | — | 152.0 |
| 13 | C5H11 | H | F | 0.05 | 5 | 69.4 | 74.5~75.5 | 157.5 |
| 14 | C6H13 | H | F | 0.1 | 20 | 68.0 | 81.9~83.7 | 145.1~145.7 |
| 15 | C7H15 | H | F | 0.1 | 17 | 62.7 | 65.9 | 142.0 |
| 16 | C3H7 | H | Cl | 0.2 | 20 | 75.1 | 79.0 | 191.8~192.0 |
| 17 | C4H9 | H | Cl | 0.2 | 20 | 57.2~58.2 | — | 182.0~182.5 |
| 18 | C5H11 | H | Cl | 0.1 | 10 | 62.0~63.6 | — | 183.5 |
| 19 | C6H13 | H | Cl | 0.15 | 15 | 57.6~58.6 | — | 173.4 |
| 20 | C7H15 | H | Cl | 0.2 | 20 | 56.4~57.4 | — | 173.5 |

*All compounds of these Examples have

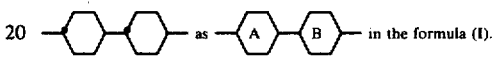 as 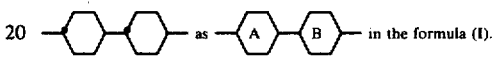 in the formula (I).

EXAMPLE 21~30

Compounds were prepared the same as in Example 1 except that, in the formula (I), R (alkyl) was varied from that of Example 1; X was varied from H to F or Cl; and Y was changed from F to H. Their yields, phase transition points, etc. are shown in Table 3.

TABLE 3

| Example | In Formula (I)* R | X | Y | Yield (g) | (%) | C-N point | Phase transition points (°C.) N-I point | |
|---|---|---|---|---|---|---|---|---|
| 21 | C3H7 | F | H | 0.9 | 6.1 | 47.3~49.3 | 93.9~94.1 | |
| 22 | C4H9 | F | H | 4.5 | 28 | 44.3~45.3 | 91.0~91.3 | |
| 23 | C5H11 | F | H | 0.9 | 7.3 | 31.3~31.7 | 101.8~102.0 | |
| 24 | C6H13 | F | H | 3.5 | 20 | 52.0~54.0 | 96.4~96.7 | |
| 25 | C7H15 | F | H | 6.5 | 38 | 39.0~39.7 | 96.4~96.7 | |
| 26 | C3H7 | Cl | H | 2.1 | 14 | 52.2 | 50.5 | (monotropic) |
| 27 | C4H9 | Cl | H | 3.3 | 20 | 57.0 | 49.7 | (monotropic) |
| 28 | C5H11 | Cl | H | 2.4 | 14 | 54.0~55.0 | 67.5 | |
| 29 | C6H13 | Cl | H | 3.0 | 17 | 57.0~57.9 | 63.5 | |
| 30 | C7H15 | Cl | H | 4.5 | 25 | 54.6~56.2 | 73.7 | |

*All compounds of these Examples have

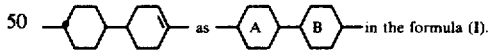 as 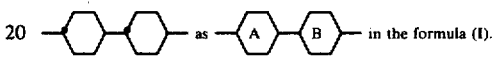 in the formula (I).

EXAMPLE 31~38

3-[4'-(Trans-4"-alkylcyclohexyl)cyclohexen-1'-yl]halogenobenzenes obtained in Examples 21~30 were reduced as in Example 11 to give 3-[trans-4'-(trans-4"-alkylcyclohexyl)cyclohexyl]halogenobenzenes as shown in Table 4. Their yields, phase transition points, etc. are shown in Table 4.

TABLE 4

| Example | In Formula (I)* R | X | Y | Yield (g) | (%) | Phase transition points (°C.) C-N point or C-S point | S-N point | N-I point |
|---|---|---|---|---|---|---|---|---|
| 31 | C3H7 | F | H | 0.1 | 11 | 54.5~56.5 | — | 92.1~92.2 |
| 32 | C4H9 | F | H | 0.15 | 15 | 55.0~56.2 | 65.0 | 87.6~ |

TABLE 4-continued

| Example | In Formula (I)* R | X | Y | Yield (g) | (%) | Phase transition points (°C.) C-N point or C-S point | S-N point | N-I point |
|---|---|---|---|---|---|---|---|---|
| 33 | $C_5H_{11}$ | F | H | 0.1 | 10 | 58.0~59.5 | 72.0~75.0 | 88.0 89.0~90.0 |
| 34 | $C_6H_{13}$ | F | H | 0.2 | 20 | 62.4 | 74.2~80.0 | 94.5 |
| 35 | $C_7H_{15}$ | F | H | 0.1 | 10 | 74.5~75.5 | — | 99.4~99.6 |
| 36 | $C_3H_7$ | Cl | H | 0.1 | 14 | 42.2~43.2 | — | 43.9 |
| 37 | $C_4H_9$ | Cl | H | 0.05 | 5 | 28.4~29.8 | — | 39.8 |
| 38 | $C_7H_{15}$ | Cl | H | 0.1 | 10 | 49.6~51.0 | — | 70.3 |

*All compounds of these Examples have

 in the formula (I).

EXAMPLES 39~41

Example 1 was repeated except that 3,4-difluorobromobenzene was used in place of 4-fluorobromobenzene to obtain 1,2-difluoro-4-[4'-(trans-4''-alkylcyclohexyl)cyclohexen-1'-yl]benzenes (compounds having

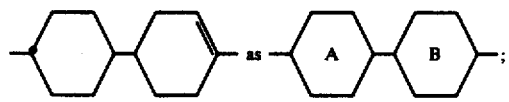

F as X and F as Y in the formula (I)) as shown in Table 5. Their yields, phase transition points, etc. are shown in Table 5.

TABLE 5

| Example | In Formula (I)* R | X | Y | Yield (g) | (%) | Phase transition points (°C.) C-N point | N-I point |
|---|---|---|---|---|---|---|---|
| 39 | $C_3H_7$ | F | F | 4.1 | 26 | 40.7~43.0 | 115.0 |
| 40 | $C_4H_9$ | F | F | 5.4 | 33 | 43.0~45.0 | 114.0 |
| 41 | $C_6H_{13}$ | F | F | 3.5 | 20 | 43.6~46.0 | 115.8 |

*All compounds of these Examples have

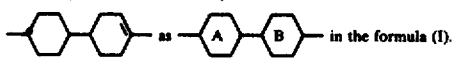 in the formula (I).

EXAMPLES 42~44

1,2-Difluoro-4-[4'-(trans-4''-alkylcyclohexyl)cyclohexen-1'-yl]benzenes obtained in Examples 39~41 were reduced as in Example 11 to give 1,2-difluoro-4-[trans-4'-(trans-4''-alkylcyclohexyl)cyclohexyl]benzenes. Their yields, phase transition points, etc. are shown in Table 6.

TABLE 6

| Example | In Formula (I)* R | X | Y | Yield (g) | (%) | Phase transition points (°C.) C-S point | S-N point | N-I point |
|---|---|---|---|---|---|---|---|---|
| 42 | $C_3H_7$ | F | F | 0.3 | 30 | 40.4 | 45.0 | 124.1~124.2 |
| 43 | $C_4H_9$ | F | F | 0.25 | 14 | 38.7 | 44.1 | 118.2 |
| 44 | $C_6H_{13}$ | F | F | 0.25 | 11 | 52.3 | 54.4 | 116.0 |

*All compounds of these Examples have

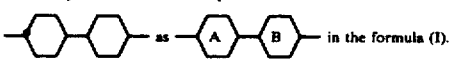 in the formula (I).

EXAMPLE 45

Preparation of 4-[4'-(4''-heptylphenyl)cyclohexen-1'-yl]fluorobenzene (a compound of the formula (I) wherein R:$C_7H_{15}$,

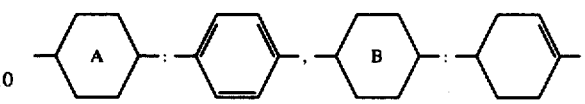

Y:H and X:F)

4-(4'-Heptylphenyl)phenol (200 g) was dissolved in ethanol (0.5 l) and a commercially available Raney nickel catalyst (20 g) was added, followed by hydrogenation at 80°~120° C. under hydrogen pressures of 30~40 Kg/cm$^2$G for 6 hours in an autoclave. The reaction was traced by gas chromatography (column: SIDC-560-10%, 2 m, 280° C.), and when the raw material was extinct, the reaction was stopped. The catalyst was filtered off from the hydrogenation product, and after ethanol was distilled off under reduced pressure, the product was dissolved in toluene (200 ml). On the other hand, metallic sodium (18.4 g) was added to toluene (400 ml), followed by heating to 110° C. and then quenching down to room temperature under high speed agitation to prepare a sodium dispersion. To this dispersion was added the above toluene solution of the hydrogenation product, followed by stirring at room temperature for one hour. The mixture was further agitated at 100° C. for 4 hours, followed by cooling and then gradually adding methanol (200 ml). The whole mixture was transferred into a separating funnel and washed twice with 10% hydrochloric acid (200 ml) and once with a saturated aqueous solution of sodium hydrogen carbonate (200 ml), followed by repeated washings with water until the water layer became neutral. The toluene layer was dried over anhydrous sodium sulfate and toluene was distilled off under reduced pressure, followed by adding n-hexane (200 ml) and standing still overnight obtain crystals of trans-4-(4'-heptylphenyl)cyclohexanol. Yield: 41.6 g, 20.4%, m.p.: 80.2°~82.5° C.

This trans-4-(4-(4'-heptylphenyl)cyclohexanol (30 g) was dissolved in acetone (1.5 l), and while the solution was kept at −3° to 0° C., a solution obtained by adding water to chromic anhydride (14.5 g) and conc. sulfuric acid (23.6 g) so as to give a volume of 50 ml, was dropwise added to the former solution over 2 hours. After completion of the reaction, the excess oxidant was decomposed by adding isopropyl alcohol, and the solution was neutralized with sodium hydrogen carbonate. The resulting precipitate was filtered off, washed with acetone (200 ml) and combined with the filtrate obtained above. Acetone was distilled off from the combination under reduced pressure, and the residue was subjected to vacuum distillation to collect a fraction of 140°~147° C./1 mmHg which corresponded to 4-(4'-heptylphenyl)cyclohexanone. Yield: 21.2 g, 71.4%.

Separately, cut metallic magnesium (0.4 g) was added to tetrahydrofuran (20 ml), and further 4-bromofluorobenzene (3.2 g) was gradually dropwise added while the temperature was kept at 30°~35° C. When about one half of the benzene was added, the reaction started, and after one hour, the magnesium dissolved to form a uniform solution which was a tetrahydrofuran solution of 4-fluorobenzenemagnesium bromide. To this solution was rapidly dropwise added a solution obtained by dissolving 4-(4'-heptylphenyl)cyclohexanone (3.3 g) in tetrahydrofuran (20 ml), while the reaction temperature was kept at 5°~10° C., followed by stirring at 35°~40° C. for one hour, thereafter carefully adding 3 N hydrochloric acid (50 ml), transferring the reaction liquid into a separating funnel, subjecting it to extraction three times with toluene (200 ml) and combining the toluene layers together, which were then washed with water until the water layer became neutral and dried over anhydrous sodium sulfate. Toluene was distilled off under reduced pressure and an oily substance remained, which was 4-[1'-hydroxy-4'-(4''-heptylphenyl)cyclohexyl]fluorobenzene. Potassium hydrogen sulfate (5 g) was added to this substance, followed by dehydration in nitrogen gas current at 160° C. for 2 hours. After cooling, toluene (200 ml) was added, potassium hydrogen sulfate was filtered off and the toluene layer was washed with water until the washing liquid became neutral. Toluene was then distilled off and the residual oily substance was recrystallized from ethanol/toluene to obtain the objective 4-[4'-(4''-heptylphenyl)cyclohexen-1'-yl]fluorobenzene as a nematic liquid crystal. Mp (C-N point): 50.7°~50.8° C., transparent point (N-I point): 71.6°~71.9° C. Yield: 1.9 g, 44.8%.

EXAMPLES 46~50

4-(4'-Heptylphenyl)phenol in Example 45 was replaced by 4-(4'-alkylphenyl)phenols having other alkyl groups to obtain 4-[4'-(4''-alkylphenyl)cyclohexen-1'-yl]fluorobenzenes. Further, 4-fluorobromobenzene was replaced by 4-chlorobromobenzene to obtain products wherein X=Cl. Their yields, phase transition points, etc. are shown together with the results of Example 45 in Table 7.

TABLE 7

| Example | In Formula (I)* | | | Yield | | Phase transition points (°C.) | |
|---|---|---|---|---|---|---|---|
| | R | X | Y | (g) | (%) | C-N point | N-I point |
| 46 | C3H7 | H | F | 4.0 | 31 | 76.3~76.5 | 81.5~81.9 |
| 47 | C4H9 | H | F | 6.4 | 40 | 52.0~52.3 | 66.5~67.1 |
| 48 | C5H11 | H | F | 5.0 | 59 | 46.1~47.2 | 74.6~74.9 |
| 49 | C6H13 | H | F | 12.1 | 56 | 50.9~51.5 | 65.8~66.0 |
| 45 | C7H15 | H | F | 1.9 | 45 | 50.7~50.8 | 71.6~71.9 |
| 50 | C6H13 | H | Cl | 2.5 | 30 | 69.7~70.3 | 100.6~100.8 |

*All compounds of these Examples have

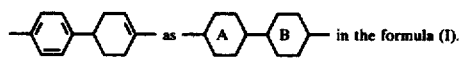 as 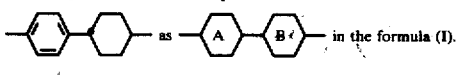 in the formula (I).

EXAMPLES 51~56

4-[4'-(4''-Alkylphenyl)cyclohexen-1'-yl]halogenobenzenes obtained in Examples 45~50 were reduced as in Example 11 to give 4-[trans-4'-(4''-alkylphenylcyclohexyl]halogenobenzenes

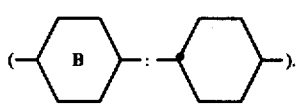

Their yields, phase transition points, etc. are shown in Table 8.

TABLE 8

| Example | In Formula (I)* | | | Yield | | Phase transition points (°C.) | |
|---|---|---|---|---|---|---|---|
| | R | X | Y | (g) | (%) | C-N point | N-I point | |
| 51 | C3H7 | H | F | 0.1 | 10 | 74.1~74.9 | 75.8~77.9 | |
| 52 | C4H9 | H | F | 0.12 | 8 | 67.6~68.0 | 58.0~58.1 | (monotropic) |
| 53 | C5H11 | H | F | 0.35 | 39 | 65.0~67.0 | 59.1~61.0 | (monotropic) |
| 54 | C6H13 | H | F | 0.55 | 22 | 54.2~54.5 | 58.9~59.0 | |
| 55 | C7H15 | H | F | 0.7 | 37 | 44.0~44.9 | 63.0~65.5 | |
| 56 | C6H13 | H | Cl | 0.3 | 30 | 66.5~66.9 | 85.5~86.5 | |

*All compounds of these Examples have

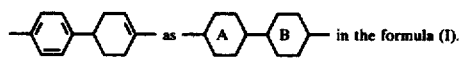 as 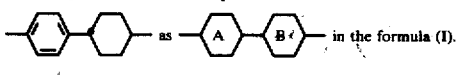 in the formula (I).

EXAMPLE 57 (USE EXAMPLE 1)

A liquid crystal composition consisting of trans-4-propyl-(4'-cyanophenyl)cyclohexane: 28% by weight, trans-4-pentyl-(4'-cyanophenyl)cyclohexane: 42% by weight, and trans-4-heptyl-(4'-cyanophenyl)cyclohexane: 30% by weight (this composition will hereinafter be referred to as liquid crystal composition A), has a nematic liquid crystal temperature range of −3° to +52° C. (Δε: +10.5). This liquid crystal composition was sealed in a TN cell (twisted nematic cell) of 10 μm thickness. Its actuation threshold voltage and saturation voltage were 1.53 V and 2.12 V, respectively. Its viscosity was 23 cp at 20° C.

To 85 parts of the above liquid crystal composition were added 15 parts of 4-[4'-(trans-4''-butylcyclohexyl)cyclohexen-1'-yl]fluorobenzene of Example 2 to obtain a liquid crystal composition (these and succeeding "Parts" being by weight). Its nematic liquid crystal temperature range became as broad as −10° to +62.5° C. Further, it was sealed in the same TN cell of 10 μm thickness as above. The resulting actuation threshold voltage (1.45 V) and saturation voltage (1.98 V) were both lower than the above values. In addition, its viscosity at 20° C. was 23 cp.

EXAMPLE 58 (USE EXAMPLE 2)

A liquid crystal composition obtained by adding 15 parts of 4-[4'-(trans-4''-butylcyclohexyl)cyclohexen-1'-yl]chlorobenzene of Example 7 to 85 parts of the liquid crystal composition A had an extended range as broad as −5° to +67.2° C. and a slightly reduced Δε of +10.0. Its threshold voltage and saturation voltage slightly rose to 1.59 V and 2.20 V, respectively, but its viscosity at 20° C. was 23.7 cp, that is, scarcely higher.

As described above, when the compounds of the present invention are used as a portion of liquid crystal compositions, they are effective for extending the nematic temperature range almost without raising the viscosity of the composition.

EXAMPLE 59 (USE EXAMPLE 3)

A liquid crystal composition obtained by adding 15 parts of 4-[4'-(trans-4''-propylcyclohexyl)cyclohexyl]fluorobenzene of Example 11 to 85 parts of the liquid crystal composition A had an extended range as broad as $-15°$ to $+62.5°$ C. and a slightly reduced dielectric anisotropy value $\Delta\epsilon$ of $+10.1$. It was sealed in the same TN cell of 10 μm thickness above. The actuation threshold voltage and saturation voltage were 1.65 V and 2.20 V, respectively. Its viscosity at 20° C. was 21 cp.

EXAMPLE 60 (USE EXAMPLE 4)

A liquid crystal composition obtained by adding 15 parts of 4-[trans-4'-(trans-4''-butylcyclohexyl)cyclohexyl]chlorobenzene of Example 17 to 85 parts of the liquid crystal composition A had an extended nematic liquid crystal temperature range as broad as $-10° \sim +67.0°$ C. and a slightly reduced $\Delta\epsilon$ of $+10.0$. Thus, its threshold voltage (1.60 V) and saturation voltage (2.25 V) slightly increased, but its viscosity at 20° C. was 23.7 cp, that is, scarcely increased.

EXAMPLE 61 (USE EXAMPLE 5)

A liquid crystal composition obtained by adding 15 parts of 3-[4'-(trans-4''-butylcyclohexyl)cyclohexen-1'-yl]fluorobenzene of Example 22 to 85 parts of the liquid crystal composition A had an extended liquid crystal temperature range as broad as $-5° \sim +59.3°$ C. Further, when it was sealed in the TN cell of 10 μm thickness as above, its actuation threshold voltage and saturation voltage were 1.67 V and 2.30 V, respectively, and its viscosity at 20° C. was 23 cp. Thus it was possible to extend the nematic temperature range almost without increasing the viscosity.

EXAMPLE 62 (USE EXAMPLE 6)

A liquid crystal composition obtained by adding 15 parts of 3-[4'-(trans-4''-pentylcyclohexyl)cyclohexen-1'-yl]chlorobenzene of Example 28 to 85 parts of the liquid crystal composition A had an extended liquid crystal temperature range as broad as $-5° \sim +54.3°$ C. Further, when it was sealed in the TN cell of 10 μm thickness as above, its actuation threshold voltage and saturation voltage were 1.71 V and 2.40 V, respectively, and its viscosity at 20° C. was 25 cp. Thus it was possible to extend the nematic temperature range almost without increasing the viscosity.

EXAMPLE 63 (USE EXAMPLE 7)

A liquid crystal composition obtained by adding 2 parts of 3-[trans-4'-(trans-4''-butylcyclohexyl)cyclohexyl]fluorobenzene of Example 32 and 8 parts of 3-[trans-4'-(trans-4''-hexylcyclohexyl)cyclohexyl]-fluorobenzene of Example 35 to 90 parts of the liquid crystal composition A had an extended nematic liquid crystal temperature range as broad as $-10° \sim +55.5°$ C. and a reduced dielectric anisotropy value $\Delta\epsilon$ of 9.9. When it was sealed in the same TN cell of 10 μm thickness as above, the actuation threshold voltage and saturation voltage were 1.57 V and 2.19 V, respectively. Its viscosity at 20° C. was 23 cp. Thus, it was possible to extend the nematic temperature range without raising the viscosity.

EXAMPLE 64 (USE EXAMPLE 8)

A liquid crystal composition obtained by adding 10 parts of 3-[trans-4'-(trans-4''-heptylcyclohexyl)cyclohexyl]chlorobenzene of Example 37 to 90 parts of the liquid crystal composition A had an extended nematic liquid crystal temperature range as broad as $-10° \sim 53.8°$ C. and a reduced dielectric anisotropy value $\Delta\epsilon$ of $+9.7$. When it was sealed in the same TN cell of 10 μm thickness as above, the actuation threshold voltage and saturation voltage were 1.60 V and 2.20 V, respectively. Its viscosity at 20° C. was 25 cp. Thus it was possible to extend the nematic temperature range without raising the viscosity very much.

EXAMPLE 65 (USE EXAMPLE 9)

A liquid crystal composition obtained by adding 15 parts of 1,2-difluoro-4-[4'-(trans-4''-propylcyclohexyl)-cyclohexen-1'-yl]benzene of Example 39 to 85 parts of the liquid crystal composition A had an extended nematic liquid crystal temperature range as broad as $-15° \sim +58°$ C., a $\Delta\epsilon$ of $+10.1$ and a viscosity at 20° C. of 23.5 cp. When this liquid crystal composition was sealed in a TN cell of 10 μm thick, the actuation threshold voltage and saturation voltage were reduced down to 1.48 V and 2.05 V, respectively. Thus, it is seen that the compound of the present invention is effective for not only extending the nematic liquid crystal temperature range but notably improving the characteristic properties of liquid crystal compositions such as improvement in the display characteristics at lower temperatures.

EXAMPLE 66 (USE EXAMPLE 10)

A liquid crystal composition obtained by adding 20 parts of 1,2-difluoro-4-[trans-4'-(trans-4''-propylcyclohexyl)cyclohexyl]benzene of Example 42 to 80 parts of the liquid crystal composition A had an extended liquid crystal temperature range as broad as $-15° \sim +61.5°$ C. and a $\Delta\epsilon$ of $+9.3$. When this liquid crystal composition was sealed in a TN cell of 10 μm thick, the actuation threshold voltage and saturation voltage both slightly increased. Its viscosity at 20° C. was 23 cp, that is, unchanged. Thus, it is seen that the compound of the present invention is very useful for extending the nematic temperature range and improving display characteristics, etc.

EXAMPLE 67 (USE EXAMPLE 11)

A liquid crystal composition obtained by adding 12.5 parts of 4-[4'-(4''-propylphenyl)cyclohexen-1'-yl]fluorobenzene of Example 46 and 12.5 parts of 4-[4'-(4''-butylphenyl)cyclohexen-1'-yl]fluorobenzene of Example 47 to 75 parts of the liquid crystal composition A, had a nematic liquid crystal temperature range of $-7° \sim +49.7°$ C. extended toward lower temperatures, and a dielectric anisotropy value $\Delta\epsilon$ of $+9.4$. When it was sealed in the same TN cell of 10 μm thickness as above, it was possible to reduce the actuation threshold voltage and saturation voltage to 1.50 V and 2.05 V, respectively. Further it was also possible to reduce the viscosity at 20° C. to 21 cp.

EXAMPLE 68 (USE EXAMPLE 12)

A liquid crystal composition obtained by adding 25 parts of 4-[trans-4'-(4''-hexylphenyl)cyclohexyl]fluorobenzene of Example 54 to 75 parts of the liquid crystal composition A had a nematic temperature range of $-5° \sim +49.4°$ C. transferred toward the lower temperature side and a dielectric anistropy value $\Delta\epsilon$ of $+8.8$. When it was sealed in the same TN cell of 10 μm thickness as above, it was possible to reduce the actuation threshold voltage and saturation voltage to 1.49 V and 2.00 V, respectively. Further it was also possible to reduce the viscosity at 20° C. to 22 cp.

What is claimed is:

1. A liquid-crystalline halogenobenzene compound expressed by the formula

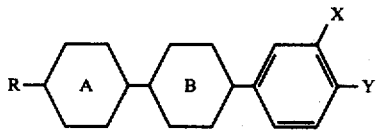

wherein R represents an alkyl group having 1 to 10 carbon atoms;

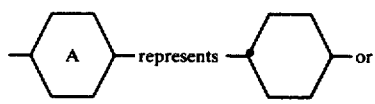

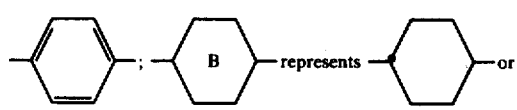

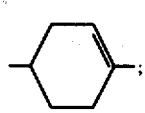

and X and Y each are H, F or Cl, at least one of X and Y being F or Cl.

2. A compound according to claim 1 wherein said

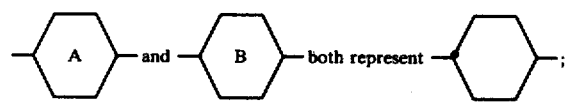

said X represents H; and said Y represents F or Cl.

3. A compound according to claim 1 wherein said

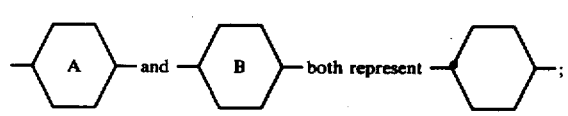

said X represents F or Cl; and said Y represents H.

4. A compound according to claim 1 wherein said

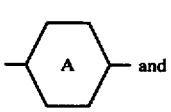

said X and Y both represent F.

5. A compound according to claim 1 wherein said

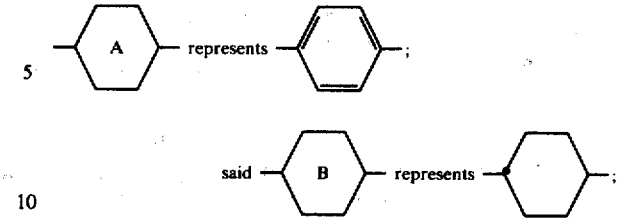

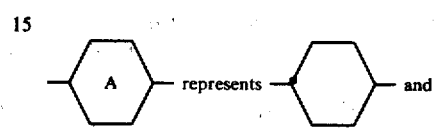

and X represents H.

6. A compound according to claim 1 wherein said

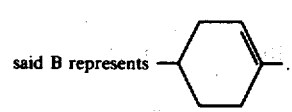

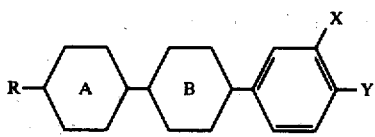

7. A liquid crystal composition comprising a mixture of compounds at least one of which is a halogenobenzene compound expressed by the formula

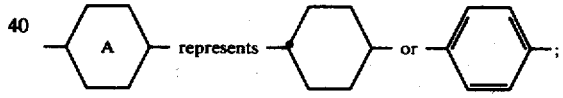

wherein R represents an alkyl group having 1 to 10 carbon atoms;

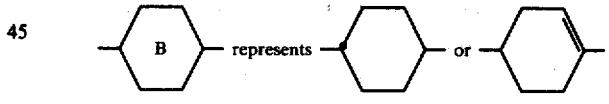

and X and Y each are H, F or Cl, at least one of X and Y being F or Cl.

8. A compound according to claim 1 wherein said

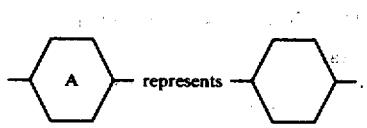

9. A compound according to claim 1 wherein said